United States Patent
Janssens

(10) Patent No.: US 7,364,764 B2
(45) Date of Patent: Apr. 29, 2008

(54) SOLUBLE ROASTED CHICORY HAVING HIGH INULIN CONTENT

(75) Inventor: Myriam Janssens, Chereng (FR)

(73) Assignee: Finaler, Lezennes (FR)

( * ) Notice: Subject to any disclaimer, the term of this patent is extended or adjusted under 35 U.S.C. 154(b) by 583 days.

(21) Appl. No.: 10/485,172

(22) PCT Filed: Jul. 29, 2002

(86) PCT No.: PCT/FR02/02716

§ 371 (c)(1),
(2), (4) Date: Mar. 3, 2004

(87) PCT Pub. No.: WO03/011042

PCT Pub. Date: Feb. 13, 2003

(65) Prior Publication Data

US 2004/0224073 A1  Nov. 11, 2004

(30) Foreign Application Priority Data

Jul. 30, 2001  (FR) .................................. 01 10202

(51) Int. Cl.
*A23F 5/00* (2006.01)

(52) U.S. Cl. ...................... 426/596; 426/431; 426/594; 426/658

(58) Field of Classification Search ................ 426/431, 426/594, 658
See application file for complete search history.

(56) References Cited

U.S. PATENT DOCUMENTS 5,840,361 A * 11/1998 Theuer et al. ............... 426/615
5,939,127 A * 8/1999 Abboud ....................... 426/572
5,958,497 A 9/1999 Grimm et al.
6,645,534 B2 * 11/2003 Hermand .................... 424/773

FOREIGN PATENT DOCUMENTS

EP  0 824 109 A  2/1998
FR  2 245 293 A  4/1975
GB  1 452 819  10/1976
WO  WO 96/24256  8/1996

OTHER PUBLICATIONS

Cieslak, Jadwiga: "Some physico-chemical and technological aspects of the production of soluble chicory. Part I." *Prace Inst. Lab. Bad. Przem. Spozyw.* vol. 35, 1981, pp. 113-122, p. 116-118, table 1.

Clarke, R.: "Coffee vol. 5: Related beverages" 1987, *Elsevier Applied Science*, London, p. 46-p. 53; table 10. p. 38, table 5.

Pazola, Z. et al.: "Changes in carbohydrates during the production of coffee substitute extracts, especially in the roasting process." *Food chemistry 1979 Inst. Of Human Nutr.*, Agric. Acad., Mazowiecka 48, 60-623 Poznan, Poland, vol. 4, No. 1, pp. 41-52.

Pordab, Zofia: "Some physico-chemical and technological aspects of the production of soluble chicory. Part II." *Prace Inst. Lab. Bad. Przem. Spozyw.*, vol. 35, 1981, pp. 123-130; p. 130, table 3.

Database FSTA 'Online! International food information service (IFIS), Franfurt/Main, DE; Gulyaev, V.N. et al: "Use of aluminium tubes for packaging soluble chicory in paste form." Database accession No. 79-3-06-f0274. Abstract. & Konservnaya I Ovoshchesushil'Naya Promyshlennost 1978 Vses. Nauchno-Issled. Inst. Konservnoi Promyshlennosti I Spetsial 'Noi Pishchevoi Tekhnologii, USSR, No. 6, 1978, pp. 26-29.

Database FSTA 'Online! International food information service (IFIS), Franfurt/Main, DE; Westerdijk, C.E.: "Chicory (*Cichorium intybus* L. var.*Sativus*) for inulin production." Database accession No. 97-1-07-j0149. Abstract. & Agro Food Industry Hi-Tech, vol. 8, No. 1, 1997, pp. 5-6, Lelystad, Netherlands.

* cited by examiner

*Primary Examiner*—Anthony Weier
(74) *Attorney, Agent, or Firm*—Weingarten, Schurgin, Gagnebin & Lebovici LLP

(57) ABSTRACT

The soluble roasted natural chicory in powder form with a high content of inulin and fructo oligosaccharides (FOS) about from 50% to 60% by weight relative to the dry matter. Its color index as measured by the absorbance of a 1% solution at 500 nm lies in the range 0.4 to 0.7. In addition, its combined content of fructose plus glucose is greater than 5%, preferably lying in the range 7% to 9% by weight relative to the dry matter.

2 Claims, No Drawings

SOLUBLE ROASTED CHICORY HAVING HIGH INULIN CONTENT

This application is a 371 national phase filing of PCT/FR02/02716 filed Jul. 29, 2002, and claims priority to a French application No. 01/10202 filed Jul. 30, 2001.

The present invention relates to the food industry, and in particular to soluble roasted chicory usable as a food ingredient for feeding man or animals.

BACKGROUND OF THE INVENTION

The work of G. R. Gibson and M. B. Roberfroid has set out the concept of food ingredients known as "prebiotic". These are ingredients that are not digestible, but that serve selectively to stimulate the growth and/or the activity of a specific bacterium or of a small number of species of colon bacteria, thus improving the health of the consumer. In order to be "prebiotic", the food ingredient must satisfy the following conditions. It must not be hydrolyzed or absorbed in the upper portion of the digestive tract. It must constitute a selective substrate for the specific bacteria or a small number of favorable colon bacteria, whose development and/or metabolism is stimulated. Consequently, it must be capable of favorably modifying the composition of the colon microflora. Finally, it must induce systemic effects that stimulate health of the consumer.

Until now, the only food ingredients that have been recognized and used as satisfying the above conditions are fructanes or oligofructoses. With reference to the 1995 article by Gibson and Roberfroid, the term "fructo oligosaccharide" (FOS) designates oligofructoses that are polymerized up to degree 9 at most, and the term "inulin" designates an oligofructose having a higher degree of polymerization, lying in the range 10 to 60, and on average 12.

However, in the literature, the generic term "inulin" is used frequently to designate inulin proper and also fructo oligosaccharides (FOS). It is in this generic sense that the term "inulin" is used in the present specification.

Carbohydrates are not digestible in the upper portion of the tractus; they are not subject to the enzymatic action of amylases, saccharases, maltases amongst others. Thus, inulin and FOS pass from the ileum to the colon without being absorbed, and they are considered in this respect as constituting alimentary fibers. However, although they are not metabolized by digestive enzymes, they nevertheless present calorific value. Intestinal microflora can metabolize them into short-chain fatty acids (aliphatic organic acids) and into lactate (organic acid). The calorific value of inulin and of fructo oligosaccharides (FOS) lies in the range 4.2 kilojoules per gram (kj/g) to 6.3 kj/g, i.e. in the range 1 kilocalorie per gram (kcal/g) to 1.5 kcal/g.

Furthermore, the bifidostimulating effect has been demonstrated by experiments both in vitro and in vivo for fructo oligosaccharides and for inulin. In particular, experiments carried out by the biomedical sciences department of the Tokyo Agriculture Faculty have shown an improvement in fecal microflora after administering 8 grams (g) of fructo oligosaccharides for 2 weeks. The number of bifidobacteria in stools was multiplied by ten. The mean pH of the stools was lowered by 0.3 and the authors observed an improvement in lipid metabolism. It has thus been shown that so-called "prebiotic" ingredients are effective in changing the composition of intestinal microflora, such that favorable bacteria predominate over species that are potentially dangerous.

It is known that inulin is one of the components of chicory, possibly representing as much as 70% of the dry matter of chicory root. This root is indeed used for extracting inulin. However, concerning the use of chicory as a food ingredient, the conventional method comprises a plurality of steps of dehydration, roasting, extraction, and atomization, during which the inulin content decreases and can become zero. More precisely, the inulin becomes degraded into fructose, particularly under the combined action of temperature and moisture. That is what makes it possible to obtain the particular taste, aroma, flavor, and color of conventional soluble roasted chicory which is used a food ingredient.

According to the Applicant, the soluble roasted chicory obtained by the conventional method—referred to below as "conventional" chicory—has an inulin content of about 18% to 19%, and in any case less than 20%.

OBJECTS AND SUMMARY OF THE INVENTION

The object of the present invention is to propose a soluble roasted natural chicory in powder form having a high inulin content, greater than 40% by weight relative to the dry matter.

This inulin content is preferably about 50% to 60% by weight relative to the dry matter. When the content is of that order, consuming a traditionally prepared bowl on the basis of such chicory having high inulin content gives the consumer about 10% of the alimentary fiber required for one day.

Another object of the invention is to propose a method of producing soluble roasted natural chicory in powder form which presents high inulin content. In conventional manner, the method comprises the following steps:

a) dehydrating fresh roots to obtain cossettes;

b) roasting the cossettes;

c) cooling and pounding the roasted cossettes;

d) extracting chicory by passing hot water over the roasted and pounded cossettes; and e) atomizing the chicory extract.

In manner characteristic of the invention, the roasting is performed at a temperature of about 130° C. with a reduced moisture content in the roaster.

It should be observed that, in the conventional method, roasting is performed at a temperature of about 145° C. Thus, in the invention, it is selected to work at a temperature that is abnormally low, and with a low moisture content, so as to avoid those reactions which normally take place, i.e. rupture of the glucide chain and the production of free sugars. Conventional roasting does indeed have the effects of conferring on chicory its particular flavor which is the result of the initial bitterness of the chicory, of producing free sugars, and of the sugars condensing between one another or with amino acids. The fact that, in accordance with the invention, less free sugar is produced, the sugars condense less amongst one another or with amino acids, and there is less degradation of the bitter principles (sesquiterpene lactones), leads to bitterness being greater than with conventional chicory. However, this bitterness is not necessarily a drawback, some consumers can accept it spontaneously given the benefit provided by the presence of alimentary fibers in large quantities. In addition, this bitterness can easily be masked by mixing the high inulin content chicory of the invention with other components, such as coffee, chocolate, or some other usual food component.

DETAILED DESCRIPTION OF THE INVENTION

The reduced moisture content during roasting is obtained in two ways which are preferably combined. In the first, no water is added during roasting, including during the stage referred to as "picketing" which is the essential stage during which the cossettes of dry chicory root finish cooking, and in which the ball of the roaster continues to turn for about 20 minutes (min) after the first stage of progressive heating up to a temperature of about 140° C. to 150° C.

In the second technique, water content is reduced in the roaster by allowing the water vapor that is produced to escape.

The inulin content of the chicory of the invention may also depend, in part, firstly on the variety that is selected and secondly on the soil. Concerning which variety to select, it is appropriate to retain amongst available seeds those varieties that have potential in terms of high yield, high dry matter content, and high inulin content. The greater the percentage of soluble dry matter, the greater not only the percentage of inulin, but also the degree to which said inulin is polymerized. Particularly preferred varieties are known respectively as Orchies and Turquoise, coming from the supplier Florimond Desprez, and it is preferable to select fresh roots coming from a plant variety whose potential in terms of yield, dry matter content, and inulin content is equivalent to or greater than the potential of said reference varieties.

Concerning the soil, it is preferable to sow early in order to allow inulin chains to become long, and for that purpose it is preferable to select ground that is sandy or sandy and alluvial. The favorable climate is maritime, i.e. warm and wet.

The soluble roasted natural chicory in powder form which is obtained by the above method differs also in certain other characteristics.

Proposals have already been made in U.S. Pat. No. 5,958,497 for a soluble chicory powder having an inulin content by weight lying in the range 30% to 65%. However, in that document, the intended purpose was to eliminate the drawbacks of the conventional chicory production method implementing steps of roasting, extraction, and drying, which are said to lead to unsatisfactory sensory properties and to excessive absorption of moisture. The purpose of obtaining a high inulin content is to reduce the moisture absorption of the resulting chicory. The method implemented in that document absolutely does not correspond to the conventional steps of producing chicory, since in particular there is no roasting step. According to that novel method, chicory is initially extracted by one or other of the extraction methods, i.e. extracting water from kiln-dried chicory or extracting by pressing chicory roots. The chicory extract is heated in a tubular reactor in order to hydrolyze a fraction of the inulin contained in the extract so as to increase the reducing sugar content of the extract. Thereafter the extract coming from the extractor is dried in order to obtain a powder. The powder is passed through an extruder which is heated so that the powder is subjected to heat treatment for 5 min at a temperature lying in the range 180° C. to 250° C. in order to obtain a caramelized substance at the outlet from the extruder. The caramelized substance is cooled and then ground in order to obtain ground soluble chicory.

The resulting substance differs in its composition which has an inulin content by weight lying in the range 40% to 65%, and it also has a reducing sugar content lying in the range 4% to 6%, with a combination of fructose plus glucose of less than 5%; in addition, the soluble chicory powder has a color index lying in the range 1.0 to 2.5, which range of values covers the indices usually obtained for conventional chicory (from 1.5 to more than 2).

In comparison, the chicory that is naturally rich in inulin which is obtained by the method of the invention has a color index as measured under the same conditions as those of document U.S. Pat. No. 5,958,497 which is much lower since it lies in the range 0.4 to 0.7. Concerning reducing sugars, the average content is greater than 10%.

Concerning the combination of fructose and glucose, the content is greater than 5%, normally lying in the range 7% to 9%.

Contrary to that which is described in document U.S. Pat. No. 5,958,497, the method of the invention implements the same steps and the same equipment as in the conventional method of producing soluble chicory suitable for use as a food ingredient. The merit of the Applicant lies in organizing the operating conditions of the conventional method for the purpose of obtaining soluble roast chicory having a high inulin content, greater than 40%, which is found to be sufficient to convince the consumer that there is a beneficial provision of alimentary fiber with all of the advantages that the presence of such fibers contribute to the alimentary equilibrium of the consumer, and in particular to intestinal transit. The teaching of document U.S. Pat. No. 5,958,497 clearly cannot lead to the substance or the method of the invention since firstly it goes against using the conventional method that includes roasting, thus leading to a substance that has not been roasted, and secondly the presence of inulin is desired in order to avoid the soluble powder presenting moisture-absorbing characteristics. The fresh roots used for producing chicory having high inulin content in the manner described below come from seeds of the Orchies variety.

The fresh roots were initially dehydrated in order to obtain root pieces referred to as "cossettes". The cossettes were introduced into a roaster loaded to about 1000 kilograms (kg) and adapted to evacuate water vapor. The roaster was subjected to progressive indirect heating from a gas burner up to a temperature of about 130° C. Once that temperature was reached, the gas supply was turned off. The picketing time was 25 min to 35 min, i.e. the time during which the roaster ball continued to turn, thereby allowing the cossettes to finish off being cooked. At the end of that stage, the roasted cossettes were emptied into a cooler, being subjected for a determined length of time to a forced flow of air. After cooling, the roasted cossettes were pounded. After pounding, extraction could begin. During this stage, water was caused to flow at above 80° C. as a counterflow over the pounded chicory grains. The chicory extract, i.e. the recovered liquor, was filtered, and centrifuged prior to being atomized.

The roasted and soluble natural chicory powder obtained in that way contained 98% by weight dry matter. In addition, by weight relative to said dry matter, it contained 59.1% inulin, 4.3% saccharose, 7.3% free fructose, and about 0.5% free glucose.

Its color index was obtained by measuring the absorbance of a 1% chicory solution at 500 nanometers (nm) and produced a value lying in the range 0.598 to 0.634.

In addition the reducing sugar content was 10.3 g per 100 g of chicory (measured by the Bertrand method, results expressed in terms of glucose).

In comparison, a roasted and soluble natural chicory powder obtained by the conventional method contained on average and by weight relative to the weight of dry matter: 18.7% inulin, 2.4% saccharose, 22.5% free fructose, and 3.1% free glucose. In addition, its color index as obtained under the same conditions had a value lying in the range 1.567 to 2.005. Thus, the soluble roasted natural chicory in powder of the present invention presents characteristics in terms of composition and color index that distinguish it clearly from those of conventional chicory, and also from those of the chicory described in U.S. Pat. No. 5,958,497.

The invention claimed is:

1. Soluble roasted natural chicory in powder form, with a high content of inulin and fructo oligosaccharides (FOS) about from 50% to 60% by weight relative to the dry matter content of said chicory, wherein the combined content of fructose plus glucose in said chicory is in the range of 7% to 9% by weight relative to the dry matter content of said chicory.

2. Chicory according to claim 1, of color index measured by the absorbance of a 1% solution of said chicory at 500 nm lies in the range 0.4 to 0.7.

* * * * *